US012741998B2

(12) United States Patent
Tavernier et al.

(10) Patent No.: US 12,741,998 B2
(45) Date of Patent: Sep. 22, 2026

(54) TARGETING OF HUMAN INTERFERON ANTAGONISTS

(71) Applicants: VIB VZW, Ghent (BE); UNIVERSITEIT GENT, Ghent (BE); CENTRE NATIONAL DE LA RECHERCHE SCIENTIFIQUE, Paris (FR); UNIVERSITÉ DE MONTPELLIER, Montpellier (FR); CENTRE HOSPITALIER REGIONAL UNIVERSITAIRE DE MONTPELLIER, Montpellier (FR)

(72) Inventors: Jan Tavernier, Balegem (BE); Lennart Zabeau, Ghent (BE); Gilles Uze, Montpellier (FR); Franciane Paul, Montpellier (FR); Yann Bordat, Montpellier (FR); Genevieve Garcin, Montpellier (FR)

(73) Assignees: VIB VZW, Ghent (BE); UNIVERSITEIT GENT, Ghent (BE); CENTRE NATIONAL DE LA RECHERCHE SCIENTIFIQUE, Paris (FR); UNIVERSITE DE MONTPELLIER, Montpellier (FR); CENTRE HOSPITALIER REGIONAL UNIVERSITAIRE DE MONTPELLIER, Montpellier (FR)

( * ) Notice: Subject to any disclaimer, the term of this patent is extended or adjusted under 35 U.S.C. 154(b) by 1216 days.

(21) Appl. No.: 17/171,433

(22) Filed: Feb. 9, 2021

(65) Prior Publication Data

US 2021/0238247 A1 Aug. 5, 2021

Related U.S. Application Data

(63) Continuation of application No. 16/008,686, filed on Jun. 14, 2018, now Pat. No. 10,947,288, which is a continuation of application No. 15/642,989, filed on Jul. 6, 2017, now Pat. No. 10,072,059, which is a continuation of application No. 14/905,348, filed as application No. PCT/EP2014/063976 on Jul. 1, 2014, now Pat. No. 9,732,135.

(30) Foreign Application Priority Data

Jul. 19, 2013 (EP) .................................... 13306045

(51) Int. Cl.
*C07K 14/56* (2006.01)
*C07K 16/28* (2006.01)

(52) U.S. Cl.
CPC .......... *C07K 14/56* (2013.01); *C07K 16/2869* (2013.01); *C07K 2317/22* (2013.01); *C07K 2317/569* (2013.01); *C07K 2319/00* (2013.01); *C07K 2319/33* (2013.01); *C07K 2319/74* (2013.01)

(58) Field of Classification Search
None
See application file for complete search history.

(56) References Cited

U.S. PATENT DOCUMENTS

| | | | |
|---|---|---|---|
| 5,914,254 A | 6/1999 | Mascarenhas et al. | |
| 8,980,267 B2 * | 3/2015 | Grewal .................. | A61P 35/00 424/134.1 |
| 9,139,634 B2 | 9/2015 | Morrison et al. | |
| 2010/0172868 A1 | 7/2010 | Morrison et al. | |
| 2010/0297076 A1 | 11/2010 | Morrison et al. | |
| 2011/0104112 A1 | 5/2011 | Morrison et al. | |
| 2011/0224407 A1 | 9/2011 | Langer et al. | |
| 2011/0274658 A1 | 11/2011 | Silver et al. | |
| 2013/0183298 A1 | 7/2013 | Le et al. | |
| 2014/0348789 A1 | 11/2014 | Tavernier et al. | |
| 2015/0139951 A1 | 5/2015 | Grewal et al. | |

FOREIGN PATENT DOCUMENTS

| | | | |
|---|---|---|---|
| WO | 9102754 | A1 | 3/1991 |
| WO | 2006053883 | A1 | 5/2006 |
| WO | 2006115800 | A2 | 11/2006 |
| WO | 2008014612 | A1 | 2/2008 |
| WO | 2008124086 | A2 | 10/2008 |
| WO | 2009003145 | A1 | 12/2008 |
| WO | 2009039409 | A1 | 3/2009 |
| WO | 2010036918 | A2 | 4/2010 |

(Continued)

OTHER PUBLICATIONS

Pan, Manjing, et al. "Mutation of the IFNAR-1 receptor binding site of human IFN-α2 generates type I IFN competitive antagonists." Biochemistry 47.46 (2008): 12018-12027 (Year: 2008).*
Hammer, Ohad. "CD19 as an attractive target for antibody-based therapy." mAbs vol. 4,5 (2012): 571-7. doi:10.4161/mabs.21338 (Year: 2012).*
Yu, Renren, Bo Zhu, and Degao Chen. "Type I interferon-mediated tumor immunity and its role in immunotherapy." Cellular and Molecular Life Sciences 79.3 (2022): 191 (Year: 2022).*
Wang, Kemeng, Guoqing Wei, and Delong Liu. "CD19: a biomarker for B cell development, lymphoma diagnosis and therapy." Experimental hematology & oncology 1 (2012): 1-7 (Year: 2012).*
El-Sayes, Nader et al. "IFNAR blockade synergizes with oncolytic VSV to prevent virus-mediated PD-L1 expression and promote antitumor T cell activity." Molecular therapy oncolytics vol. 25 16-30. Mar. 16, 2022, doi:10.1016/j.omto.2022.03.006 (Year: 2022).*

(Continued)

*Primary Examiner* — Misook Yu
*Assistant Examiner* — Lia E Taylor
(74) *Attorney, Agent, or Firm* — Morgan, Lewis & Bockius LLP

(57) ABSTRACT

The present invention relates to a fusion protein, comprising a cytokine antagonist and a targeting moiety, preferably an antibody or anti-body like molecule. In a preferred embodiment, the cytokine antagonist is a modified cytokine which binds to the receptor, but doesn't induce the receptor signalling. The invention relates further to a fusion protein according to the invention for use in treatment of cancer and immune- or inflammation-related disorders.

4 Claims, 5 Drawing Sheets

(56) References Cited

FOREIGN PATENT DOCUMENTS

| | | | |
|---|---|---|---|
| WO | 2010066740 | A1 | 6/2010 |
| WO | 2011020783 | A2 | 2/2011 |
| WO | 2011029870 | A1 | 3/2011 |
| WO | 2012170072 | A1 | 12/2012 |
| WO | 2013059885 | A2 | 5/2013 |
| WO | 2013107791 | A1 | 7/2013 |
| WO | 2013134138 | A1 | 9/2013 |

OTHER PUBLICATIONS

Acres, B., et al., "Fusokine Interleukin-2/Interleukin-18, a Novel Potent Innate and Adaptive Immune Stimulator with Decreased Toxicity", Cancer Res., vol. 65, No. 20, (2005), pp. 9536-9546.

Baba, M., et al., "Identification of CCR6, the Specific Receptor for a Novel Lymphocyte-Directed CC Chemokine LARC", The Journal of Biological Chemistry vol. 272, No. 23, (1997), pp. 14893-14898.

Camacho, N.P., et al., "Structure of an Interleukin-1β Mutant With Reduced Bioactivity Shows Multiple Subtle Changes in Conformation That Affect Protein-Protein Recognition", Biochemistry, vol. 32, No. 34, (1993), pp. 8749-8757.

Coulstock, E., et al., "Liver-Targeting of Interferon-Alpha with Tissue Specific Domain Antibodies." PLOS ONE, vol. 8, No. 2, (2013), pp. 1-11.

De Bruyn, M., et al., "Antibody-Based Fusion Proteins to Target Death Receptors in Cancer", Cancer Letters, vol. 332, (2013), pp. 175-183.

Dijkmans, R., et al., "Murine Interferon-Y/Interleukin-1 Fusion Proteins Used as Antigens for the Generation of Hybridomas Producing Monoclonal Anti-Interleukin-1 Antibodies", Cytokine, vol. 3, No. 2, (1991), pp. 134-140.

Dimitrov, D. S., "Engineered CH2 Domains (Nanoantibodies)", mAbs, Landes Bioscience, vol. 1, No. 1, (2009), pp. 26-28.

Frey, K., et al., "Antibody-Based Targeting of Interferon-Alpha to the Tumor Neovasculature: A Critical Evaluation", Integrative Biology, vol. 3, (2011), p. 468-478.

Garcin, G., et al., "High Efficiency Cell-Specific Targeting of Cytokine Activity", Nature Communications, (2014), pp. 1-9.

Holler, N., et al: "Two Adjacent Trimeric Fas Ligands are Required for Fas Signaling and Formation of a Death-Inducing Signaling Complex", Molecular and Cellular Biology, vol. 23, No. 4, (2003), pp. 1428-1440.

Huang, T., et al., "A Trimeric Anti-HER2/neu ScFv and Tumor Necrosis Factor-[alpha] Fusion Protein Induces HER2/Neu Signaling and Facilitates Repair of Injured Epithelia", The Journal of Pharmacology and Experimental Therapeutics, vol. 316, No. 3, (2006), pp. 983-991.

International Search Report and Written Opinion in PCT/EP2013/050787, dated Jun. 14, 2013.

International Search Report and Written Opinion PCT/EP2014/063976, dated Oct. 29, 2014.

International Search Report and Written Opinion PCT/EP2014/064227, dated Feb. 5, 2015.

International Search Report and Written Opinion PCT/EP2014/064283, dated Oct. 1, 2014.

International Search Report and Written Opinion PCT/EP2014/065554, dated Oct. 30, 2014.

Krippner-Heidenreich, A., et al: "Single-Chain TNF, a TNF Derivative with Enhanced Stability and Antitumoral Activity", The Journal of Immunology, vol. 180, (2008), pp. 8176-8183.

Masci, P. et al., "New and Modified Interferon alfas: Preclinical and Clinical Data", Current Oncology Reports, vol. 5, (2003), pp. 108-113.

Pan, M., et al., "Mutation of the IFNAR-1 Receptor Binding Site of Human IFN-[alpha]2 Generates Type I IFN Competitive Antagonists", Biochemistry, vol. 47, (2008), pp. 12018-12027.

Penafuerte, C., et al., "The Human Ortholog of Granulocyte Macrophage Colony-Stimulating Factor and Interleukin-2 Fusion Protein Induces Potent Ex Vivo Natural Killer Cell Activation and Maturation", Cancer Res, vol. 69, No. 23, (2009), pp. 9020-9028.

Rafei, M., et al., "A MCP1 Fusokine with CCR2-Specific Tumoricidal Activity", Molecular Cancer, vol. 10, No. 121, (2011), pp. 1-11.

Rafei, M., et al., "An Engineered GM-CSF-CCL2 Fusokine Is a Potent Inhibitor of CCR2-Driven Inflammation as Demonstrated in a Murine Model of Inflammatory Arthritis", The Journal of Immunology, vol. 183, (2009), pp. 1759-1766.

Roisman, LC., et al., "Structure of the Interferon-Receptor Complex Determined by Distant Constraints from Double Mutant Cycles and Flexible Docking", PNAS, vol. 98, No. 23, (2001), pp. 13231-13236.

Rovero S et al., "Insertion of the DNA for the 163-171 Peptide of Il 1β Enables a DNA Vaccine Encoding p185neu to Inhibit Mammary Carcinogenesis in Her-2/neu Transgenic BALB/c Mice", Gene Therapy, vol. 8, (2001), pp. 447-452.

Schutyser, E., et al., "The CC Chemokine CCL20 and its Receptor CCR6", Cytokine & Growth Factor Reviews, vol. 14, (2003), pp. 409-426.

Weber, H., et al., "Single Amino Acid Changes that Render Human IFN-[alpha]2 Biologically Active on Mouse Cells", The EMBO Journal, vol. 6, No. 3, (1987), pp. 591-598.

Bork "Powers and Pitfalls in Sequence Analysis: The 70% Hurdle", Genome Research, vol. 10 (2000), pp. 398-400.

Bork et al., "Go hunting in sequence databases but watch out for the traps." Trends in Genetics vol. 12 (1996), pp. 425-427.

Wells, "Additivity of mutational effects in proteins." Biochemistry, vol. 29, No. 37, (1990), pp. 8509-8517.

Ngo et al., "The Protein Folding Problem and Tertiary Structure Prediction", Edited by: Mertz et al., (Birkhauser, Boston), (1994), pp. 492-495.

* cited by examiner

TARGETING OF HUMAN INTERFERON ANTAGONISTS

The present invention relates to a fusion protein, comprising a cytokine antagonist and a targeting moiety, preferably an antibody or antibody like molecule. In a preferred embodiment, the cytokine antagonist is a modified cytokine which binds to the receptor, but doesn't induce the receptor signalling. The invention relates further to a fusion protein according to the invention for use in treatment of cancer or for use in treatment of autoimmune diseases. Cytokines are critical mediators of defence mechanisms against microbial invasion and tumorigenesis. However, their production and activities must be tightly regulated to prevent an excessive activity that can culminate in the uncontrolled inflammation and tissue injury, as characteristically observed with many autoimmune diseases.

Rheumatoid arthritis is the classic example of an autoimmune disease where TNFα, IL-1, and IL-6 play a prominent role in the recruitment of lymphocytes and other types of leukocytes that mediate a progressive joint destruction. TNF inhibitors have been shown to decrease symptoms, slow disease progression, and improve the quality of life for many patients with rheumatoid arthritis (Moreland, 2009). Similarly, a mAb neutralizing IL-12 and IL-23 (ustekinumab) provides a potential therapy for psoriasis (Elliott et al., 2009) and a recombinant human IL-1 receptor antagonist, (anakinra, Kineret™), first approved by the FDA in 2001 for the treatment of rheumatoid arthritis, is a promising agent for the treatment of many IL-1-mediated autoinflammatory diseases (Goldbach-Mansky, 2009).

Several lines of evidence support the notion that overproduction of type I interferon by plasmacytoid dendritic cells is the primary pathogenesis of several autoimmune diseases, including systemic lupus erythematosus, a multi-system autoimmune disease that affects skin, kidney, musculoskeletal, and hematologic tissues, and Sjogren's syndrome, a disease characterized by the destruction of glands producing tears and saliva and which impacts 1-3% of the human population. Indeed, if the natural IFN production is not regulated properly, the ensuing prolonged type I IFN exposure can drive autoantibody production which promotes the onset of systemic autoimmune disease (Kiefer et al., 2012). Accordingly, novel therapeutics targeting type I IFN have been developed. For instance, two monoclonal antibodies which neutralize IFNα (Sifalimumab and Rontalizumab) are currently in clinical trials (McBride et al., 2012; Merrill et al., 2011) and a type I IFN antagonist has also been designed (Pan et al., 2008), (PCT/US2009/056366).

IL17A is the best characterized member of the IL17 family of cytokines. This pleiotropic cytokine interacts with a receptor composed of IL17RA and IL17RC subunits. The IL17RA chain is ubiquitously expressed, including haematopoietic, immune, epithelial, endothelial cell types, as well as fibroblasts. IL17A is typically produced by Th17 cells upon activation by a subset of cytokines including IL-1, IL-6, IL-21 and TGFβ, and propagates early inflammatory signals that serve to bridge innate and adaptive immune responses. IL17 is a potent activator of neutrophils and plays an important role in the immune defence against various extracellular pathogens. It is also well established that IL17A promotes autoimmune pathologies (Gaffen, 2009; Shen & Gaffen, 2008). Brodalumab, Secukinumab and Ixekizumab target the IL17A/IL17R axis for treatment of auto-immune diseases such as psoriasis and Crohn's disease. All may inflict adverse side effects including enhanced risk of infections (Hueber et al. 2012; Spuls & Hooft, 2012).

Specific targeting of IL17A antagonists to selected cell types such as airway epithelium (asthma), astrocytes (multiple sclerosis), synoviocytes and monocytes/macrophages (rheumatoid arthritis) or keratinocytes (psoriasis) may therefore offer a significant advantage over completely antagonising IL17 function.

IL1α and ILβ are the founding members of the IL1 cytokine family. Both are pleiotropic and function through a ubiquitously expressed receptor complex composed of IL-1 receptor type-I (IL-1RI) and IL-1 receptor accessory protein (IL-1RAcP). Overactivation of this IL-1 axis is associated with many human pathologies including rheumatoid arthritis (RA), chronic obstructive pulmonary disease (COPD), asthma, inflammatory bowel diseases, multiple sclerosis, atherosclerosis and Alzheimer's disease. Many immune cells of different lineages are activated by IL-1, including innate immune cells such as dendritic cells, macrophages and neutrophils, and also cells involved in the adaptive immune response including naïve, Th17 and CD8+ T cells, and B cells (reviewed in Sims and Smith, 2010). Recombinant human IL-1RA (IL1 receptor antagonist, aka anakinra) can be used to treat rheumatoid arthritis and is 20 being evaluated for use in a wide spectrum of autoinflammatory diseases (Dinarello, 2011). One of the major side effects of prolonged treatment with anakinra is however the increased occurrence of infections. Selectively antagonising of IL-1 activity on only a subset of (immune) cells therefore may offer a safer alternative. It can be envisaged that targeted inhibition of IL-1 action on selected innate immune cells, leaving its activity on the T cell compartment intact, may still show efficacy for the treatment of inflammatory diseases, without affecting the host defence against pathogens.

Although the IL-7-related cytokine TSLP (thymic stromal lymphopoietin) is best studied in the context of promoting Th2 responses, it is now clear that it functions on various immune and non-immune cell types (reviewed in Roan et al., 2012). Its receptor is composed of the IL-7Rα, which is shared with IL-7, and the widely expressed TSLPRα, also known as CRLF2 (Pandey et al., 2000). TSLP promotes Th2-type inflammation by acting on several distinct cell types, including dendritic cells, CD4 and CD8 T cells, B cells, NKT cells, mast cells, eosinophils and basophils. It supports host defence against helminth parasites, but can contribute to allergic inflammation, and antagonising TSLP was suggested as a treatment for allergic diseases. Conversely, TSLP can have a protective role in inflammatory diseases driven by exacerbated Th1 and Th17 responses, such as Inflammatory Bowel Disease (reviewed in He and Geha, 2010 and Roan et al., 2012). It was recently also found that mutations in the TSLPRα are associated with cancer, including leukemias with poor prognosis (Harvey et al., 2010; Yoda et al., 2010; Ensor et al., 2011), and TSLP levels are correlated with breast cancer progression (Olkhanud et al., 2011) and reduced survival in pancreatic cancer (De Monte et al., 2011). Selective targeting of TSLP antagonists to selected tumor cell types therefore may offer a selective antitumor strategy, and additional modulation by targeted antagonism of selected immune cells may be used to further optimise such strategy. Similar approaches could also be undertaken for non-malignant diseases.

The main problem with the therapeutic approaches aiming to neutralize cytokine actions is that the cytokine antagonists are not targeted towards cells or tissues that are specifically involved in the onset of the autoimmune or autoinflammatory diseases. For example, It is easily foreseeable that a long term systemic neutralization of type I IFN activity by a monoclonal antibody or an IFN receptor antagonist carry an important risk in term of viral infection susceptibility and tumor development since type I IFN is a family of proteins essential in the control of viral infections and for establishing immune responses, particularly those controlling cancer cell growth (Gajewski et al., 2012). Similarly, it is expected that a systemic neutralization of IL-1 activity will impact the expansion, effector function, tissue localization, and memory response of antigen-cytotoxic T cells during immune responses (Ben-Sasson et al., 2013).

Surprisingly we found that specific targeting of the cytokine antagonist to a subset of target cells allows reaching the therapeutic effect, without having the negative side effects of systemic cytokine antagonist application. The invention is exemplified by targeting the action of a type I IFN antagonist to specific cell types expressing a given cell surface marker. Such a method is applied to the design and construction of a targeted IFN antagonist that inhibits the action of endogenous IFN specifically on the cell subset culpably involved in the onset of autoimmune diseases, leaving the other cells and organs fully responsive.

Although not yet approved, oncolytic viruses are advancing through clinical trials (Russell et al., 2012). Oncolytic viruses are often designed for having attenuated replication capacity in normal tissues by engineering their sensitivity to the normal cellular interferon-mediated antiviral responses. An example is an oncolytic vesicular stomatitis virus coding for interferon β (Naik et al., 2012). The therapeutic effect of such viruses is expected to be a consequence of the defect of the IFN response exhibited by many tumor cells. However, the genetic heterogeneity of tumors that impact the IFN response is highly variable and impairs the efficacy of virus-mediated tumor lysis (Naik and Russell, 2009). Therefore, by inhibiting the IFN response specifically in tumor cells, a tumor-targeted IFN antagonist would permit the specific destruction of tumor cells by an oncolytic virus.

A first aspect of the invention is a fusion protein comprising a cytokine antagonist and a targeting moiety consisting of an antibody or an antibody like molecule. A cytokine antagonist as used here can be any cytokine antagonist known to the person skilled in the art, including but not limited to a soluble receptor, a cytokine binding antibody or a mutant cytokine. Preferably said cytokine antagonist is a mutant cytokine, even more preferably a mutant which binds to the receptor, but is not or only weakly inducing the cytokine signalling. Preferably, the affinity of the mutant for the receptor is comparable to that of the wild type cytokine, even more preferable it has a higher affinity; preferably the signalling induced by the mutant is less than 20% of that of the wild type, even more preferably less than 10% of that of the wild type, even more preferably less than 5%, even more preferably less than 1%. Most preferably, the binding of the mutant cytokine does not result in detectable signalling. Such mutant can act as a competitive inhibitor of cytokine signalling. An antibody or antibody like molecule as used here is a protein specifically designed to bind another molecule, preferably a proteineous molecule, and comprising the specific binding domains. As a non-limiting example, said antibody or antibody like molecule can be a heavy chain antibody (hcAb), single domain antibody (sdAb), minibody (Tramontano et al., 1994), the variable domain of camelid heavy chain antibody (VHH), the variable domain of the new antigen receptor (VNAR), affibody (Nygren et al., 2008), alphabody (WO2010066740), designed ankyrin-repeat domain (DARPins) (Stumpp et al., 2008), anticalin (Skerra et al., 2008), knottin (Kolmar et al., 2008) and engineered CH2 domain (nanoantibodies; Dimitrov, 2009). The definition, as used here, excludes the Fc tail (without the binding domains) of an antibody. Preferably, said antibody or antibody like molecule consists of a single polypeptide chain, even more preferably, said antibody is not post-translationally modified. Prost-translational modification, as used here, indicates the modifications carried out by living cell during or after the protein synthesis, but excludes modifications, preferably chemical modifications, carried out on the isolated protein such as, but not limited to pegylation Even more preferably said antibody or antibody-like molecule comprises the complementary determining regions, derived from an antibody. Most preferably, said targeting antibody or antibody-like molecule is a nanobody.

Preferably, said cytokine antagonist and said targeting moiety are connected by a linker, preferably a GGS linker. Preferably said GGS linker contains at least 5 GGS repeats, more preferably at least 10 GGS repeats, even more preferably at least 15 GGS repeats, most preferably at least 20 GGS repeats.

In a preferred embodiment, the cytokine antagonist according to the invention is an interferon antagonist; even more preferably, it is an IFNα2-R120E mutant. In another preferred embodiment, the cytokine antagonist according to the invention is an antagonist of a cytokine of the IL17 family, preferably an IL17A antagonist. In still another preferred embodiment, the cytokine antagonist according to the invention is an antagonist of the IL1 cytokine family, preferably an IL1α or ILβ antagonist. In still another preferred embodiment, the cytokine antagonist according to the invention is a TSLP antagonist.

In one preferred embodiment, the antibody or antibody-like molecule is directed against a cancer cell marker. Cancer cell markers are known to the person skilled in the art, and include, but are not limited to CD19, CD20, CD22, CD30, CD33, CD37, CD56, CD70, CD74, CD138, AGS16, HER2, MUC1, GPNMB and PMSA. Preferably, said cancer marker is CD20 or HER2. In another preferred embodiment, the antibody or antibody-like molecule is directed against a marker on an immune cell, preferably an inflammatory cytokine producing immune cell. An immune cell, as used here, is a cell that belongs to the immune system, including but not limited to monocytes, dendritic cells and T-cells. Preferably, said immune cell is a pro-inflammatory cytokine producing cell.

Markers of inflammatory cytokine producing cells are known to the person skilled in the art and include but are not limited to CD4, CD11b, CD26, sialoadhesin and flt3 receptor.

Another aspect of the invention is a fusion protein according to the invention for use in treatment of cancer. Still another aspect of the invention is a fusion protein according to the invention for use in treatment of autoimmune diseases.

Another aspect of the invention is a method to treat cancer, comprising (i) determination the type of cancer and the suitable targeting marker(s) for the cancer cells in a patient suffering from cancer (ii) providing to said patient in need of the treatment a fusion protein comprising a cytokine antagonist and a targeting moiety consisting of an antibody or an antibody-like molecule according to the invention, possibly with a suitable excipient. It is obvious for the person skilled in the art that the targeting moiety of step (ii) will be directed to the targeting marker identified in step (i). Possible cancer cell markers are known to the person skilled in the art, and include, but are not limited to CD19, CD20, CD22, CD30, CD33, CD37, CD56, CD70, CD74, CD138, AGS16, HER2, MUC1, GPNMB and PMSA.

Still another aspect of the invention is a method to treat an autoimmune disease, comprising (i) determination in a patient suffering from an autoimmune disease the suitable targeting marker(s) for the immune cells (ii) providing to said patient in need of the treatment a fusion protein comprising a cytokine antagonist and a targeting moiety consisting of an antibody or an antibody-like molecule according to the invention, possibly with a suitable excipient. Immune cells, as used here, include but are not limited to dendritic cells, CD4 and CD8 T cells, B cells, NKT cells, mast cells, eosinophils and basophils.

A: Untreated
B: hIFNα2. 2 PM
C: hIFNα2. 2 μM+2HCD25-20×GGS-hIFNα2-R120E. 1 μg/ml
D: hIFNα2. 2 μM+2HCD25-20×GGS-hIFNα2-R120E. 0.1 μg/ml
E: hIFNα2. 2 μM+2HCD25-20×GGS-hIFNα2-R120E-R149A. 3 g/ml
F: hIFNα2. 2 μM+2HCD25-20×GGS-hIFNα2-R120E-R149A. 1 μg/ml
G: hIFNα2. 2 μM+2HCD25-20×GGS-hIFNα2-R120E-L153A. 3 μg/ml
H: hIFNα2. 2 μM+2HCD25-20×GGS-hIFNα2-R120E-L153A. 1 μg/ml

EXAMPLES

Materials & Methods to the Examples

Nanobody-IFN Antagonist Fusion Construction.

Using the QuikChange II-E Site-Directed Mutagenesis Kit (Agilent), the mutation R120E which abrogates IFN-IFNAR1 binding and confers the antagonistic behaviour of human IFNα2 (Pan et al., 2008), (PCT/US2009/056366), was introduced into the pMET7 SIgK-HA-4.11-His-PAS-ybbr-IFNα2 construct (PCT/EP2013/050787), which is a fusion between a nanobody against the murine leptin receptor and the human IFNα2.

Production of the Nanobody-IFN Antagonist Fusion Protein

Hek 293T cells were transfected with the protein fusion constructs using the standard lipofectamin method (Invitrogen). 48 hours after the transfection culture mediums were harvested and stored at −20° C.

Cell Lines

Hek 293T cells were grown in DMEM supplemented with 10% FCS. The HL116 clone (Uze et al., 1994) is derived from the human HT1080 cell line. It contains the firefly luciferase gene controlled by the IFN-inducible 6-16 promoter. The derived HL116-mLR10 clone which expresses the murine leptin receptor was described (PCT/EP2013/050787).

Measurement of the Luciferase Activities

Antagonistic IFN activities were measured by quantifying the inhibition of the luciferase activity induced in HL116 cells and on the HL116-mLR10 expressing the mLR by IFNα2 or IFNβ. The IC50 values were calculated using nonlinear data regression with Prism software (GraphPad). Luciferase activities were determined on a Berthold Centro LB960 luminometer using a luciferase substrate buffer (20 mM Tricine, 1.07 mM (MgCO3)4Mg(OH)2·5H2O, 2.67 mM MgSO4·7H2O, 0.1 mM EDTA, 33.3 mM dithiothreitol, 270 UM coenzyme A, 470 UM luciferin, 530 UM ATP, final pH 7.8) after 6 hr IFN stimulation.

Example 1: The Nanobody-IFNα2-R120E Fusion Protein

Figure 1:
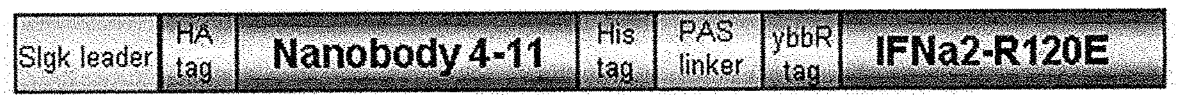
FIG. 1: Representation of the structural elements of the nanobody-hIFNα2-R120E fusion protein.

The nanobody 4-11, directed against the murine leptin receptor was fused to the IFNα2 mutant R120E as described in the materials and methods FIG. 1 shows a schematic representation of the nanobody-IFN antagonist fusion protein constructed with the nanobody 4-11 against the murine leptin receptor and the human IFNα2-R120E (numbering as in Piehler et al., 2000).

Example 2: Targeted Inhibition of IFNα Activity on mLR-Expressing Cells

Figure 2:
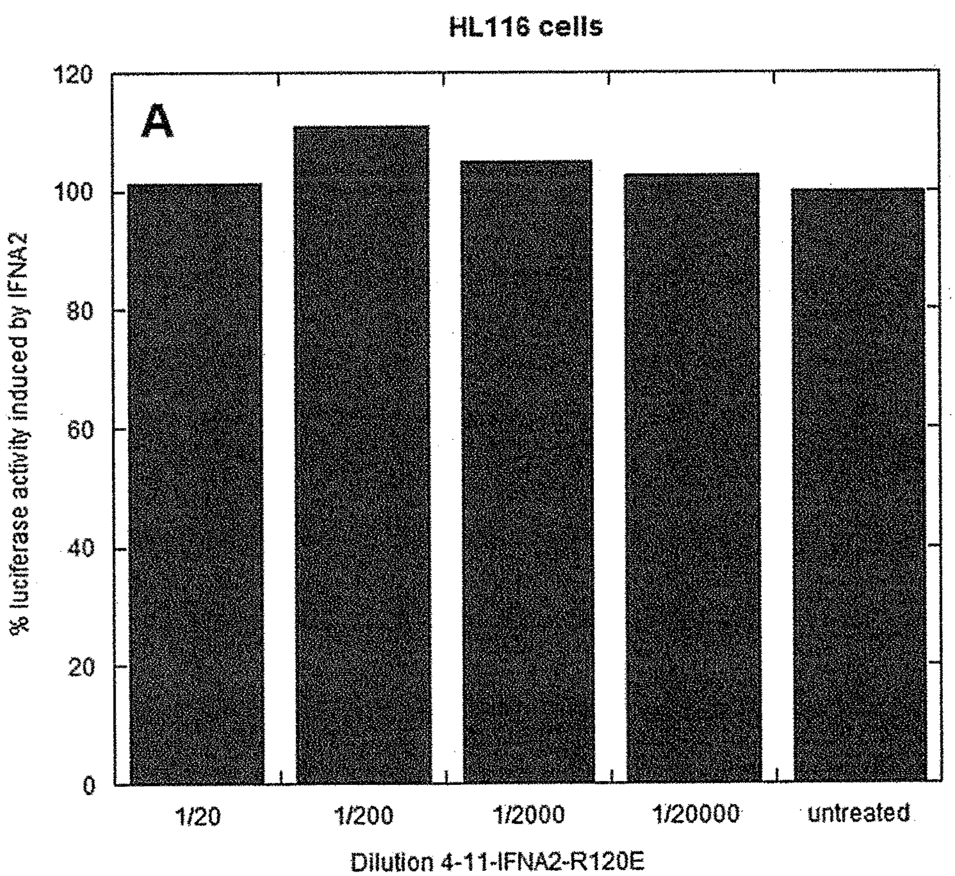
FIG. 2: Quantification of the luciferase activity induced by 10 μM hIFNα2 in the presence or absence (untreated) of the 4-11-hIFNα2-R120E fusion protein on HL116 (A) and HL116-mLR10 (B) cells.
Figure 2:
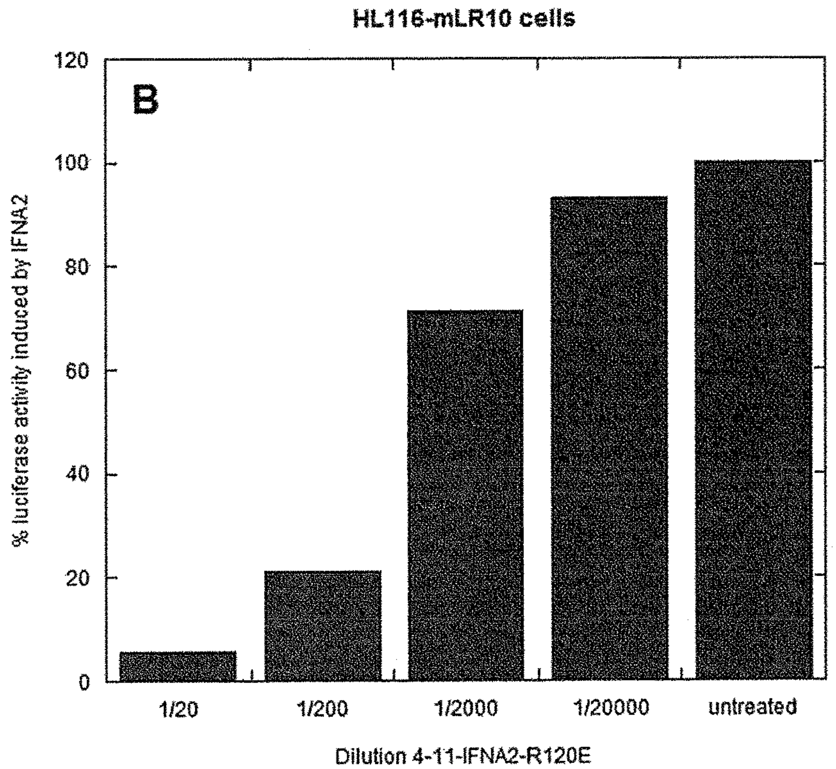

Parental HL116 cells and the derived HL116-mLR10 cells which express the mouse leptin receptor were treated for 6 hours with 10 μM IFNα2 in the presence of several dilutions of culture medium conditioned by Hek 293T cells expressing the 4-11-IFNα2-R120E fusion protein. The 10 μM IFNα2 dose was chosen because it corresponds to the IFNα2 EC50 on both cell lines. Cells were then lysed and the IFN-induced luciferase activity was quantified. At the higher concentration tested, the 4-11-IFNα2-R120E fusion protein was unable to inhibit IFNα2 action on untargeted HL116 cells (FIG. 2A). In contrast, its dose-dependent inhibition effect is clear on HL116-mLR10 cells which express the target of the 4-11 nanobody (FIG. 2B).

Example 3: Targeted Inhibition of IFNβ Activity on mLR-Expressing Cells

Among the subtypes which constitute the human type I IFN, the IFNβ shows the highest affinity for the IFNα/B receptor. We thus tested whether the 4-11-IFNα2-R120E fusion protein exerts also an antagonistic activity against IFNβ action.

Figure 3:
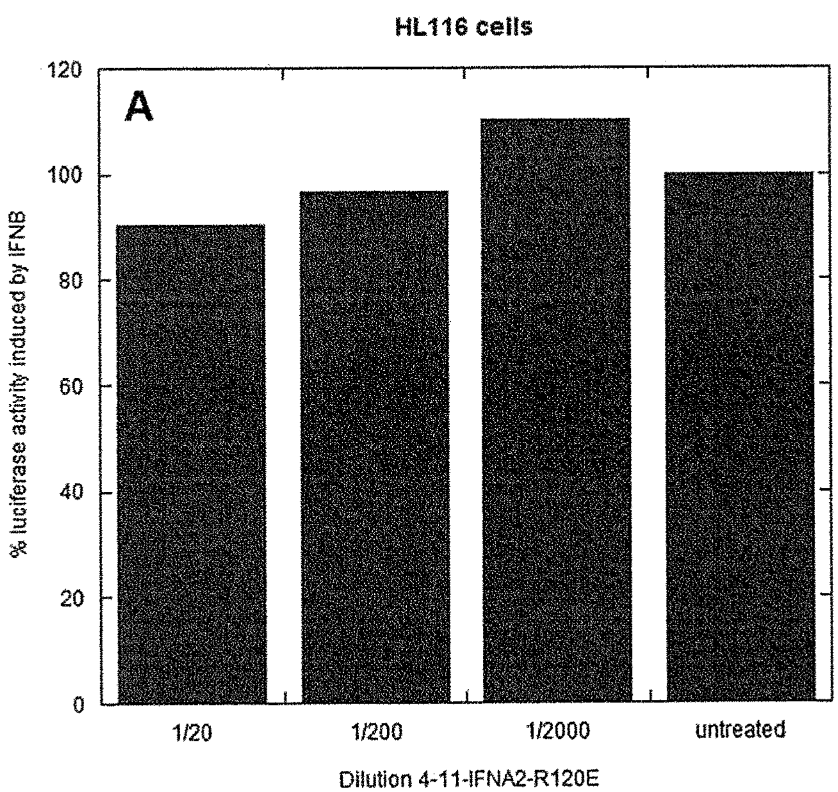
FIG. 3: Quantification of the luciferase activity induced by 1 μM IFNβ in the presence or absence (untreated) of the 4-11-hIFNα2-R120E fusion protein on HL116 (A) and HL116-mLR10 (B) cells.
Figure 3:
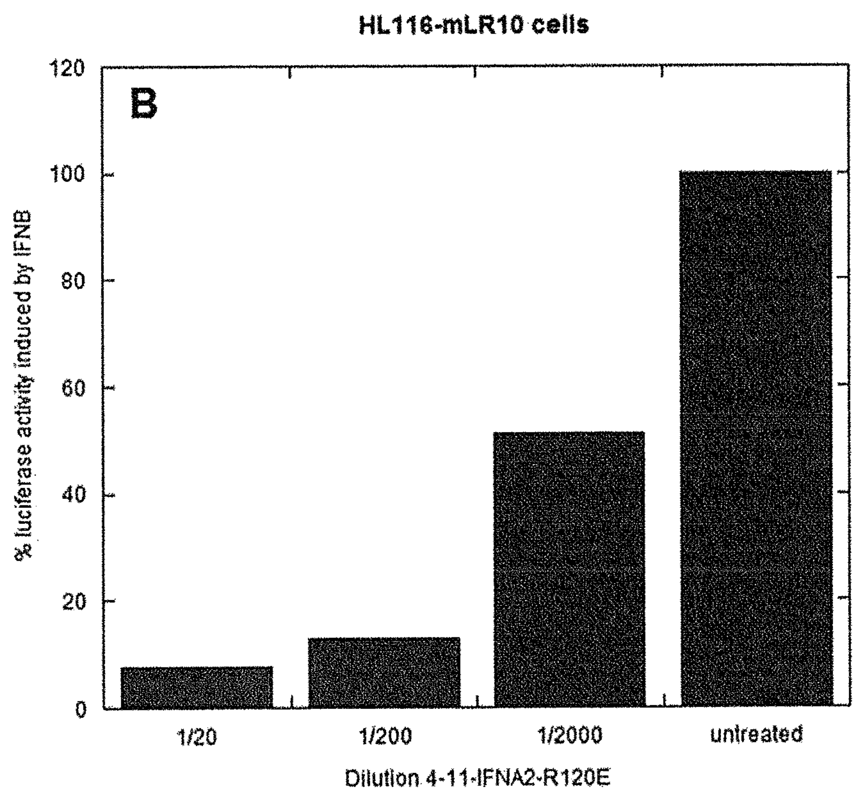

Parental HL116 cells and the derived HL116-mLR10 cells which express the mouse leptin receptor were treated for 6 hours with 1 μM IFNβ in the presence of several dilutions of culture medium conditioned by Hek 293T cells expressing the 4-11-IFNα2-R120E fusion protein. The 1 μM IFNβ dose was chosen because it corresponds to the IFNβ EC50 on both cell lines. Cells were then lysed and the IFN-induced luciferase activity was quantified. At the higher concentration tested, the 4-11-IFNα2-R120E fusion protein was unable to inhibit IFNα2 action on untargeted HL116 cells (FIG. 3A). In contrast, its dose-dependent inhibition effect is clear on HL116-mLR10 cells which express the target of the 4-11 nanobody (FIG. 3B).

Example 4. Specific Inhibition of IFNα2-Induced STAT1 Phosphorylation in B-Cells within Human Whole PBMCs The type I IFN antagonist IFNα2-R120E was fused to the anti-human CD20 nanobody 2HCD25 through a linker sequence made with 20 repeats of GGS motif. The fusion protein was produced in *E. coli* and purified by Immobilized Metal Affinity chromatography (IMAC). Human peripheral blood mononuclear cells (PBMCs) are expected to contain ≈4% of B-cells which can be characterized by the cell surface expression of CD19. The large majority of circulating B-cells are also positive for the expression of CD20.

PBMCs were isolated over ficoll gradient (histopaque-1077, Sigma-Aldrich) from blood samples of healthy donors. Cells were left untreated or were incubated for 15 minutes with 50 μM of human IFNα2 in the absence or presence of 10 μg/ml of the 2HCD25 nanobody—IFNα2-R120E fusion protein.

Cells were then fixed (BD Fix Buffer I), permeabilized (BD Perm Buffer III) and labelled with PE-labelled anti pSTAT1 (BD #612564) and APC-labelled anti human CD19 (BD #555415). FACS data were acquired using a BD FACS Canto and analyzed using Diva (BD Biosciences) software for the fluorescence associated with pSTAT1 in CD19 positive and negative cell populations.

Figure 4:
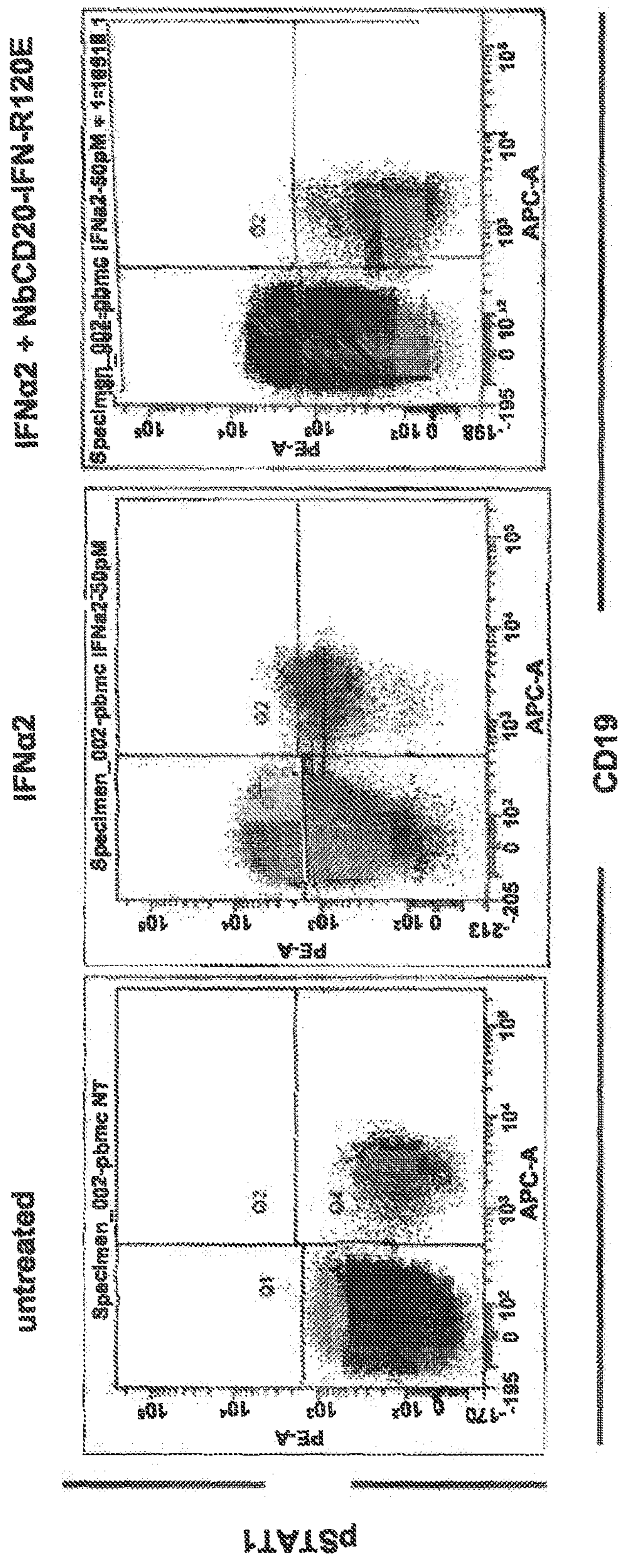
FIG. 4: FACS analysis of pY701-STAT1 in CD19 positive and negative human PBMCs left untreated (left panel), treated with 50 μM of hIFNα2 (center) or with 50 μM of hIFNα2 in the presence of the CD20-targeted IFN antagonist.

FIG. 4 shows that the IFN antagonist linked to the nanobody specific for CD20 inhibits the IFN action specifically in the major part of the B cell population, leaving intact the IFN response in the CD19 negative cell population.

Example 5. The CD20-Targeted Type I IFN Antagonist Inhibits the Antiproliferative Activity of Type I IFN Having established that the fusion protein of the 2HCD25 nanobody and IFNα2-R120E inhibits IFN-induced STAT1 phosphorylation specifically in B-cells, we tested if it can inhibit the antiproliferative activity of type I IFN. In addition, we evaluated the effect of the IFN mutations L153A and R149A that decrease the affinity of IFNα2 for IFNAR2 by a factor of 10 and 100, respectively, in combination with the inhibiting mutation R120E.

Figure 5:
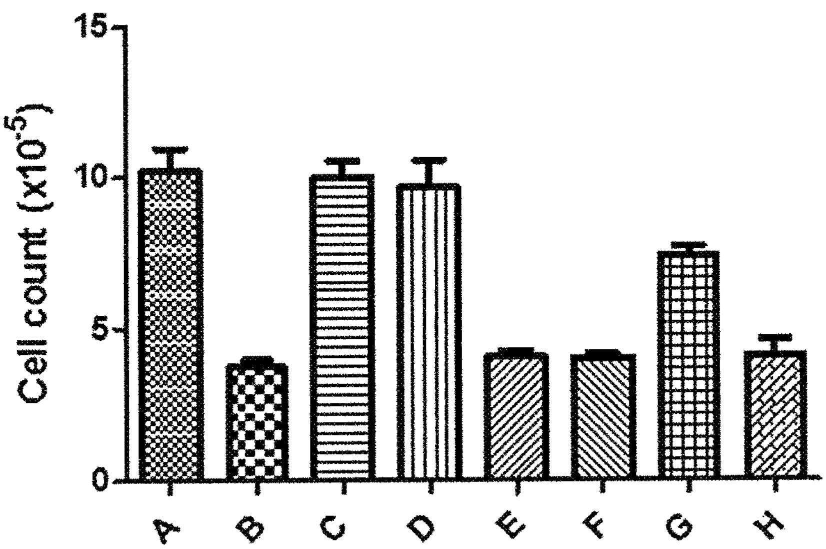
FIG. 5: Density of the Daudi cell cultures treated by the following components.

Daudi cells are a human lymphoblastoid B-cell line expressing CD20. Daudi cells were seeded at 2.0×105 cells/ml and were left untreated or cultured for 72 h in the presence of 2 pM IFNα2 alone or in combination with various CD20-targeted IFN antagonists. They were then counted to estimate the efficacy of the inhibition of proliferation induced by IFNα2. FIG. 5 shows that the CD20-targeted IFN antagonist fully inhibits the antiproliferative activity of IFNα2. It also shows that decreasing the IFN-IFNAR2 affinity decreases the antagonistic activity, proving that the inhibitory effect is indeed due to the binding of the targeted antagonist.

REFERENCES

Ben-Sasson, S. Z., Hogg, A., Hu-Li, J., Wingfield, P., Chen, X., Crank, M., Caucheteux, S., Ratner-Hurevich, M., Berzofsky, J. A., Nir-Paz, R., et al. (2013). IL-1 enhances expansion, effector function, tissue localization, and memory response of antigen-specific CD8 T cells. J Exp Med 210, 491-502.

De Monte, L., Reni, M., Tassi, E., Clavenna, D., Papa, I., Recalde, H., Braga, M., Di Carlo, V., Doglioni, C. and Protti, M. P. (2011). Intratumor T helper type 2 cell infiltrate correlates with cancer-associated fibroblast thymic stromal lymphopoietin production and reduced survival in pancreatic cancer. J. Exp Med 208, 469-478).

Dimitrov, D. S. (2009) Engineered CH2 domains (nanoantibodies). mAbs 1, 26-28.

Dinarello, C. A. (2011). Interleukin-1 in the pathogenesis and treatment of inflammatory diseases. Blood 117, 3720-3732.

Ensor, H. M., Schwab, C., Russell, L. J., Richards, S. M., Morrison, H., Masic, D., Jones, L., Kinsey, S. E., Vora, A. J., Mitchell, C. D., Harrison, C. J. and Moorman, A. V. (2011). Demographic, clinical, and outcome features of children with acute lymphoblastic leukemia and CRLF2 deregulation: results from the MRC ALL97 clinical trial. Blood 117, 2129-2136

Elliott, M., Benson, J., Blank, M., Brodmerkel, C., Baker, D., Sharples, K. R., and Szapary, P. (2009). Ustekinumab: lessons learned from targeting interleukin-12/23p40 in immune-mediated diseases. Ann N Y Acad Sci 1182, 97-110.

Gaffen, S. L. (2009). Structure and signalling in the IL-17 receptor family. Nat Rev Immunol 9, 556-567.

Gajewski, T. F., Fuertes, M. B., and Woo, S. R. (2012). Innate immune sensing of cancer: clues from an identified role for type I IFNs. Cancer Immunol Immunother 61, 1343-1347.

Goldbach-Mansky, R. (2009). Blocking interleukin-1 in rheumatic diseases. Ann N Y Acad Sci 1182, 111-123.

Harvey, R. C., Mullighan, C. G., Chen, I. M., Wharton, W., Mikhail, F. M., Carroll, A. J., Kang, H., Liu, W., Dobbin, K. K., Smith, M. A., Carroll, W. L., Devidas, M., Bowman, W. P., Camitta, B. M., Reaman, G. H., Hunger, S. P., Downing, J. R. and Willman, C. L. (2010). Rearrangement of CRLF2 is associated with mutation of JAK kinases, alteration of IKZF1, Hispanic/Latino ethnicity, and a poor outcome in pediatric B-progenitor acute lymphoblastic leukemia. Blood 115, 5312-5321.

He, R. and Geha, R. S. (2010). Thymic stromal lymphopoietin. Ann N Y Acad Sci (2010) 1183, 13-24.

Hueber, W., Sands, B. E., Lewitzky, S., Vandemeulebroecke, M., Reinisch, W., Higgins, P. D., Wehkamp, J., Feagan, B. G., Yao, M. D., Karczewski, M., Karczewski, J., Pezous, N., Bek, S., Bruin, G., Mellgard, B., Berger, C., Londei, M., Bertolino, A. P., Tougas, G. and Travis S. P. (2012). Secukinumab, a human anti-IL-17A monoclonal antibody, for moderate to severe Crohn's disease: unexpected results of a randomised, double-blind placebo-controlled trial. Gut 61, 1693-1700.

Kiefer, K., Oropallo, M. A., Cancro, M. P., and Marshak-Rothstein, A. (2012). Role of type I interferons in the activation of autoreactive B cells. Immunol Cell Biol 90, 498-504.

Kolmar, H. (2008) Alternative binding proteins: biological activity and therapeutic potential of cysteine-knot miniproteins. FEBS J. 275, 2684-2690.

McBride, J. M., Jiang, J., Abbas, A. R., Morimoto, A., Li, J., Maciuca, R., Townsend, M., Wallace, D. J., Kennedy, W. P., and Drappa, J. (2012). Safety and pharmacodynamics of rontalizumab in patients with systemic lupus erythematosus: results of a phase I, placebo-controlled, double-blind, dose-escalation study. Arthritis Rheum 64, 3666-3676.

Merrill, J. T., Wallace, D. J., Petri, M., Kirou, K. A., Yao, Y., White, W. I., Robbie, G., Levin, R., Berney, S. M., Chindalore, V., et al. (2011). Safety profile and clinical activity of sifalimumab, a fully human anti-interferon alpha monoclonal antibody, in systemic lupus erythematosus: a phase I, multicentre, double-blind randomised study. Ann Rheum Dis 70, 1905-1913.

Moreland, L. W. (2009). Cytokines as targets for anti-inflammatory agents. Ann N Y Acad Sci 1182, 88-96.

Naik, S., Nace, R., Barber, G. N., and Russell, S. J. (2012). Potent systemic therapy of multiple myeloma utilizing oncolytic vesicular stomatitis virus coding for interferon-beta. Cancer Gene Ther 19, 443-450.

Naik, S., and Russell, S. J. (2009). Engineering oncolytic viruses to exploit tumor specific defects in innate immune signaling pathways. Expert Opin Biol Ther 9, 1163-1176. Russell, S. J., Peng, K. W., and Bell, J. C. (2012), Oncolytic virotherapy. Nat Biotechnol 30, 658-670.

Nygren, P-A. (2008) Alternative binding proteins: affibody binding proteins developed from a small three-helix bundle scaffold. FEBS J. 275, 2668-2676.

Olkhanud, P. B., Rochman, Y., Bodogai, M., Malchinkhuu, E., Wejksza, K., Xu, M., Gress, R. E., Hesdorffer, C., Leonard, W. J. and Biragyn, A. (2011). Thymic stromal lymphopoietin is a key mediator of breast cancer progression. J. Immunol. 186, 5656-5662.

Pan, M., Kalie, E., Scaglione, B. J., Raveche, E. S., Schreiber, G., and Langer, J. A. (2008). Mutation of the IFNAR-1 receptor binding site of human IFN-alpha2 generates type I IFN competitive antagonists. Biochemistry 47, 12018-12027.

Pandey, A., Ozaki, K., Baumann, H., Levin, S. D., Puel, A., Farr, A. G., Ziegler, S. F., Leonard, W. J. and Lodish, H. F. (2000). Cloning of a receptor subunit required for signaling by thymic stromal lymphopoietin. Nat Immunol. 1, 59-64.

Piehler, J., Roisman, L. C. and Schreiber, G. (2000). New structural and functional aspects of the type I interferon-receptor interaction revealed by comprehensive mutational analysis of the binding interface. J. Biol. Chem 275, 40425-40433.

Roan, F., Bell, B. D., Stoklasek, T. A., Kitajima, M., Han, H. and Ziegler, S. F. (2012). The multiple facets of thymic stromal lymphopoietin (TSLP) during allergic inflammation and beyond. J Leuk Biol, 91, 877-886.

Shen, F. and Gaffen, S. L. (2008). Structure-function relationships in the IL-17 receptor: implications for signal transduction and therapy. Cytokine 41, 92-104.

Sims, J. E. and Smith, D. E. (2010). The IL-1 family: regulators of immunity. Nat Rev Immunol 10, 89-102.

Skerra, A. (2008) Alternative binding proteins: anticalins-harnessing the structural plasticity of the lipocalin ligand pocket to engineer novel binding activities. FEBS J. 275, 2677-2683.

Spuls, P. I. and Hooft, L. (2012). Brodalumab and ixekizumab, anti-interleukin-17-receptor antibodies for psoriasis: a critical appraisal. Br J Dermatol 167, 710-713.

Stump, M. T., Binz, H. K., Amstutz, P. (2008) DARPins: a new generation of protein therapeutics. Drug iscov. Today 13, 695-701.

Tramontano, A., Bianchi, E., Venturini, S., Martin, F., Pessi, A and Sollazzo, M. (1994) The making of the minibody: an engineered beta-protein for the display of conformationally constrained peptides. J. Mol. Recognition 7, 9-24.

Uze, G., Di Marco, S., Mouchel-Vielh, E., Monneron, D., Bandu, M. T., Horisberger, M. A., Dorques, A., Lutfalla, G., and Mogensen, K. E. (1994). Domains of interaction between alpha interferon and its receptor components. J Mol Biol 243, 245-257.

Yoda, A., Yoda, Y., Chiaretti, S., Bar-Natan, M., Mani, K., Rodig, S. J., West, N., Xiao, Y., Brown, J. R., Mitsiades, C., Sattler, M., Kutok, J. L., DeAngelo, D. J., Wadleigh, M., Piciocchi, A., Dal Cin, P., Bradner, J. E., Griffin, J. D., Anderson, K. C., Stone, R. M., Ritz, J., Foà, R., Aster, J. C., Frank, D. A., Weinstock, D. M. (2010). Functional screening identifies CRLF2 in precursor B-cell acute lymphoblastic leukemia. Proc Natl Acad Sci USA 107, 252-257

The invention claimed is:

1. A method for treating cancer comprising providing to a subject in need thereof an effective amount of a composition comprising a fusion protein, the fusion protein consisting of (i) an interferon antagonist, (ii) a variable domain of camelid heavy chain antibody (VHH) or a variable domain of new antigen receptor (VNAR), and (iii) a linker connecting interferon antagonist and the VHH or VNAR, wherein the interferon antagonist is a human IFNα2 comprising an R120E mutation and wherein the VHH or VNAR is directed to CD19, and wherein the cancer comprises cells expressing a CD19 cancer marker, wherein the interferon antagonist binds to the IFNα2 receptor but does not induce signaling at the IFNα2 receptor, and wherein the method further comprises providing to the subject an oncolytic virus.

2. The method of claim 1, wherein the human IFNα2 further comprises a second mutation that decreases binding activity of the interferon antagonist.

3. The method of claim 2, wherein the second mutation is R149A.

4. The method of claim 3, wherein the fusion protein further comprises a linker connecting the interferon antagonist and the VHH or VNAR.

* * * * *